(12) United States Patent
Teng et al.

(10) Patent No.: US 11,014,877 B2
(45) Date of Patent: May 25, 2021

(54) ETHER-BRIDGED DICATION, IONIC LIQUID ELECTROLYTE AND CHARGE STORAGE DEVICE THEREOF

(71) Applicant: NATIONAL CHENG KUNG UNIVERSITY, Tainan (TW)

(72) Inventors: Hsisheng Teng, Tainan (TW); I-wen Sun, Tainan (TW); Hsin-Chieh Huang, Tainan (TW); Yung-Che Yen, Tainan (TW); Jui-Cheng Chang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 16/660,830

(22) Filed: Oct. 23, 2019

(65) Prior Publication Data

US 2020/0048190 A1 Feb. 13, 2020

Related U.S. Application Data

(63) Continuation of application No. 15/415,902, filed on Jan. 26, 2017, now abandoned.

(30) Foreign Application Priority Data

Sep. 12, 2016 (TW) .................................. 105129628

(51) Int. Cl.
| | | |
|---|---|---|
| C07C 311/48 | (2006.01) | |
| C07D 233/64 | (2006.01) | |
| H01G 11/58 | (2013.01) | |
| H01G 11/62 | (2013.01) | |

(52) U.S. Cl.
CPC .......... *C07C 311/48* (2013.01); *C07D 233/64* (2013.01); *H01G 11/58* (2013.01); *H01G 11/62* (2013.01); *Y02E 60/13* (2013.01)

(58) Field of Classification Search
CPC ................................ H01G 11/58; H01G 11/62
See application file for complete search history.

(56) References Cited

U.S. PATENT DOCUMENTS 9,293,786 B1 * 3/2016 Krishnan .......... H01M 10/0564

OTHER PUBLICATIONS

Zafer et al, "Dicationic bis-imidazolium molten salts for effective dye sensitized solar cells:Synthesis and photovoltaic propeties", Electrochimia Acta. 54, May 13, 2009, pp. 5709-5714.*
Kim et al, "Novel thixotropic gel electrolytes based on dicationic bis-imidazolium salts for quasi-solid-state dye-sensitized solar cells", Journal of Power Sources, 175, 2009, pp. 692-697.*
Huang et al, "An ether bridge between cations to extend the applicability of ionic liquids in electric doble layer capacitors", J. Mater. Chem. A, 2016, 4, 19160, Nov. 26, 2016.*

* cited by examiner

*Primary Examiner* — C Melissa Koslow
(74) *Attorney, Agent, or Firm* — Soroker Agmon Nordman

(57) ABSTRACT

An ether-bridged dication is provided with two monovalent cations bonded via a carbon chain having ether group(s). The ether-bridged dication, monovalent cations, and anions are contained together within an ionic liquid electrolyte which is applied to a charge storage device. The ether-bridged dication, the ionic liquid electrolyte, and the charge storage device have operational abilities at room temperatures or below, and a reachable working potential of 3.5 V.

2 Claims, 6 Drawing Sheets

ETHER-BRIDGED DICATION, IONIC LIQUID ELECTROLYTE AND CHARGE STORAGE DEVICE THEREOF

CROSS REFERENCE TO RELATED APPLICATIONS

This application is a continuation application of U.S. patent application Ser. No. 15/415,902, filed on Jan. 26, 2017 now abandoned, and claims the priority of Taiwan Patent Application No. 105129628, filed on Sep. 12, 2016, the disclosure of which is incorporated herein by reference.

FIELD OF THE INVENTION

The present invention relates to a dication and an ionic liquid electrolyte, and a charge storage device, and in particular relates to an ether-bridged dication, an ionic liquid electrolyte containing the ether-bridged dication without an organic solvent, and a charge storage device assembled by the ionic liquid electrolyte so that it is workable at a temperature below 0° C.

BACKGROUND OF THE INVENTION

An ionic liquid electrolyte is generally composed by monovalent cation or dication together with specific anions and a medium, and applied to a charge storage device such as a capacitor or battery. For ionic conductivity at room temperature or below, the most ionic liquid electrolyte needs an additional organic antifreeze agent; otherwise, an organic solvent is required for being a medium and adjusting the fluidity and viscosity of the ionic liquid electrolyte. However, the organic solvent generally has a high volatility, which is unstable for electronic components so that the possibility of problematic occurrences is increased; for example, explosion or fire may occur when overheating. If no organic antifreeze agent or organic solvent is used, the ionic liquid electrolyte cannot maintain its fluid state at low temperatures, especially at temperatures below 5° C., which does not work properly to provide ionic conductivity. Therefore, in order to improve the safety of the ionic liquid electrolyte and extend the temperature range applicable for electronic devices, it is necessary to improve the composition of the ionic liquid electrolyte without any organic solvents and further provide excellent ionic conductivity at room temperatures or below.

It is therefore necessary to provide an ether-bridged dication, an ionic liquid electrolyte, and a charge storage device, in order to solve the problems existing in the conventional technology as described above.

SUMMARY OF THE INVENTION

A primary object of the present invention is to provide an ether-bridged dication and an ionic liquid electrolyte thereof. The ether-bridged dication is formed by two monovalent cations connected through a carbon chain having ether group(s). Therefore, the ether group can provide higher electron density to form a hydrogen bond or the like with cations, so as to improve the chemical stability of the ionic liquid electrolyte, thereby enhancing the ionic conductivity of the ionic liquid electrolyte. In addition, an organic antifreeze agent and an organic solvent are not required for the ionic liquid electrolyte. Only a small amount of the ether-bridged dication is added, and the ionic liquid electrolyte can be operated at room temperatures or below. Usage safety can also be improved.

Another object of the present invention is to provide a charge storage device assembled by the abovementioned ionic liquid electrolyte, having the advantages of a higher potential window and operability in a wide temperature range.

To achieve the above objects, the present invention provides a ether-bridged dication with two monovalent cations, $X_1$ and $X_2$ bonded through a carbon chain having at least one ether group, having the molecular structure given as follows:

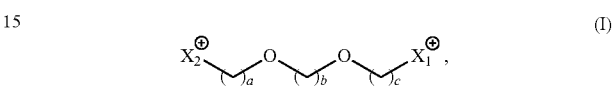

(I)

wherein X1 and X2 are independently selected from a quaternary ammonium cation, a sulfonium cation, and a phosphonium cation; and each of a, b and c is an integral selected from 1 to 10.

In one embodiment of the present invention, the quaternary ammonium cation is selected from an imidazolium cation, a pyrrolium cation, a pyridinium cation, a pyrazolium cation, a benzimidazolium cation, an indolium cation ($C_8H_8N^+$), a carbazolium cation, a quinolium cation, a pyrrolidinium cation, a piperidium cation, and an alkyl ammonium cation.

In one embodiment of the present invention, the sulfonium cation is an alkyl sulfonium cation.

In one embodiment of the present invention, the phosphonium cation is an alkyl phosphonium cation.

In one embodiment of the present invention, the ether-bridged dication is

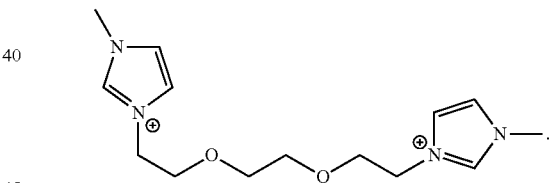

To achieve the above objects, another embodiment according to the present invention provides an ionic liquid electrolyte, comprising the abovementioned ether-bridged dication; at least one monovalent cation; and at least one anion; wherein the ionic liquid electrolyte is formed without organic solvents.

In one embodiment of the present invention, the ether-bridged dication is 2-20 wt % of the ionic liquid electrolyte.

In one embodiment of the present invention, the monovalent cation is selected from a quaternary ammonium cation, a sulfonium cation, and a phosphonium cation.

In one embodiment of the present invention, the anion is selected from $[BF_4]^-$, $[PF_6]^-$, a Bis(fluorosulfonyl)imide anion, and a Bis(trifluorosulfonyl)imide anion.

To achieve the above objects, a further embodiment according to the present invention provides a charge storage device comprising the abovementioned ionic liquid electrolyte.

In one embodiment of the present invention, the charge storage device has a specific capacitance of more than 160 F/g at −20° C.

In one embodiment of the present invention, the charge storage device has a reachable working potential at 3.5 V.

DETAILED DESCRIPTION OF THE PREFERRED EMBODIMENTS

The structure and the technical means adopted by the present invention to achieve the above and other objects can be best understood by referring to the following detailed description of the preferred embodiments. Furthermore, if there is no specific description in the invention, singular terms such as "a", "one", and "the" include the plural number. For example, "a compound" or "at least one compound" may include a plurality of compounds, and the mixtures thereof. If there is no specific description in the invention, "%" means "weight percentage (wt %)", and the numerical range (e.g., 10%~11% of A) contains the upper and lower limit (i.e., 10%≤A≤11%). If the lower limit is not defined in the range (e.g., less than, or below 0.2% of B), it means that the lower limit may be 0 (i.e., 0%≤B≤0.2%). The proportion of "weight percent" of each component can be replaced by the proportion of "weight portion" thereof. The abovementioned terms are used to describe and understand the present invention, but the present invention is not limited thereto.

According to one embodiment, the present invention provides an ether-bridged dication with two monovalent cations, X1 and X2, bonded through a carbon chain having at least one ether group, having the molecular structure given as follows:

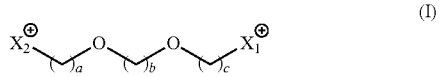

(I)

The abovementioned X1 and X2 are independently selected from a quaternary ammonium cation, a sulfonium cation, and a phosphonium cation; and each of a, b and c is an integral selected from 1 to 10. That is, $X_1$ can be the same as or different from $X_2$. Furthermore, $X_1$ has a position for bonding to the carbon chain having the ether group(s), and $X_2$ also has a position for bonding to the carbon chain. The carbon chain with the ether group(s) can be provided with alkyl substituents without specific limitations thereto.

In one embodiment of the present invention, the sulfonium cation is an alkyl sulfonium cation.

In one embodiment of the present invention, the phosphonium cation is an alkyl phosphonium cation.

According to one embodiment, the present invention provides an ionic liquid electrolyte, in addition to the ether-bridged dication as above-mentioned, comprising at least one monovalent cation and at least one anion. Preferably, the ionic liquid electrolyte is formed without organic solvents. The ionic liquid electrolyte has excellent fluidity so that it can work at a temperature below 0° C. to expand the operational range of the electrochemical devices. In one embodiment of the present invention, the ether-bridged dication is preferably 2-20% by weight of the ionic liquid electrolyte, for example, 2, 5, 10, or 15 w.t. %, but it is not limited thereto. Moreover, the monovalent cation is selected from a quaternary ammonium cation, a sulfonium cation, and a phosphonium cation. The anion mainly serves as a charge balancer for the ionic liquid electrolyte, such as

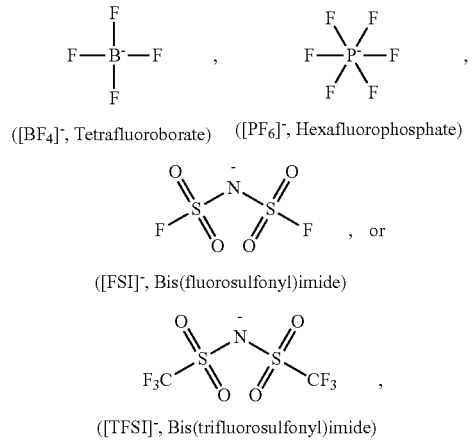

but it is not limited thereto.

Figure 1:
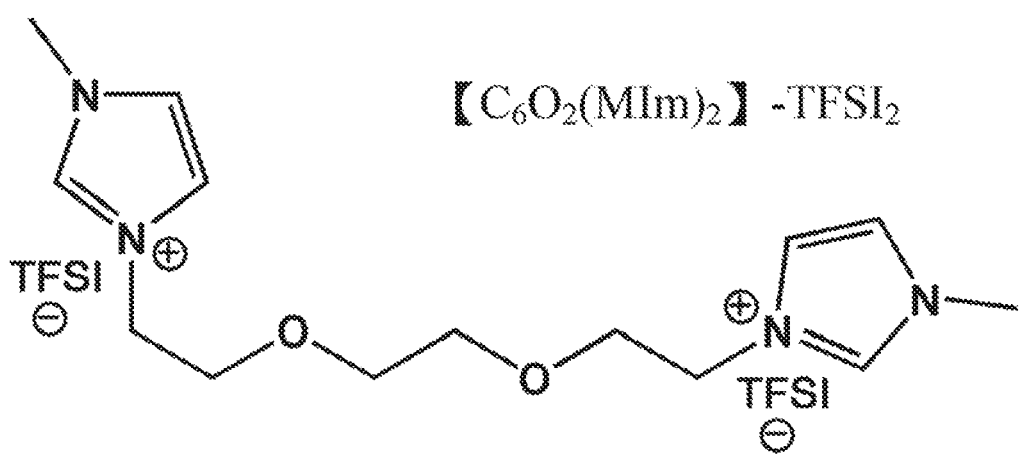
FIG. 1 shows a chemical structure of an ether-bridged dication (EMIm-TFSI) according to the present invention.
Figure 2:
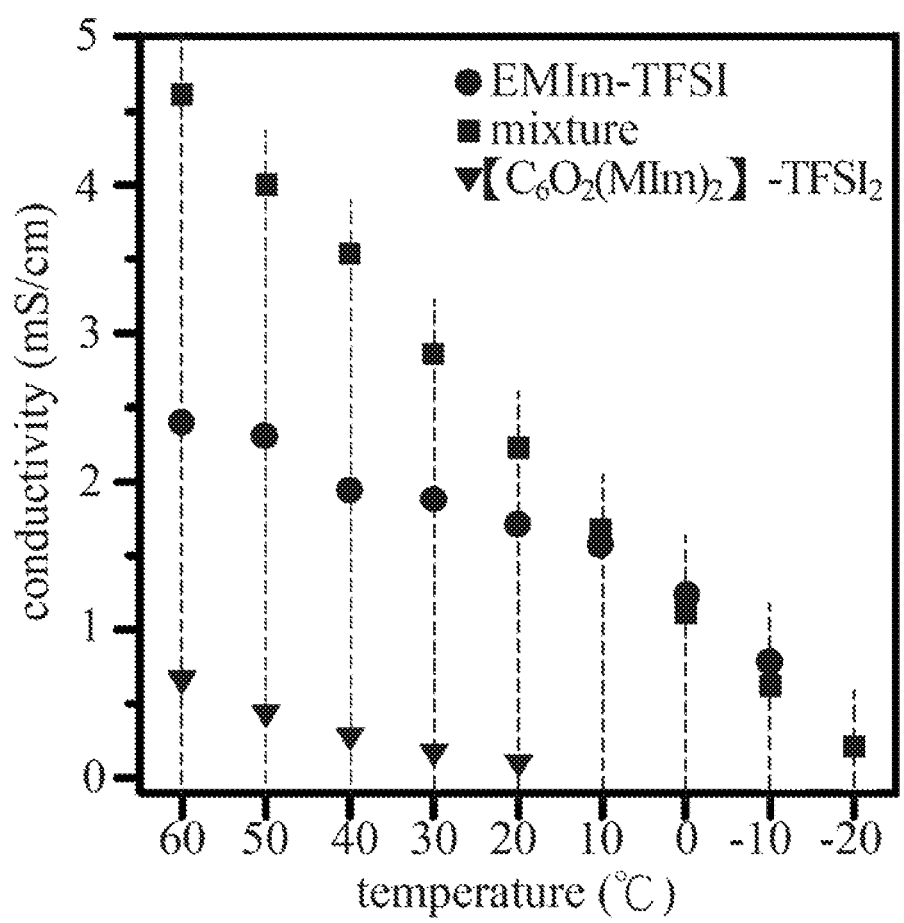
FIG. 2 shows ionic conductivity of an ionic liquid electrolyte (EMIm-TFSI+[$C_6O_2(MIm)_2$]) according to one embodiment of the present invention compared with EMIm-TFSI and [$C_6O_2(MIm)_2$]-$TFSI_2$.

Refer to FIG. 1, which shows an ether-bridged dication and the suitable anion according to one embodiment of the present invention. The ether-bridged dication can be produced by, for example, heating N-methylimidazole and 1,2-bis(2-chloroethoxy)ethane in methanol to 100° C. for reaction, and then replacing the chloride ion with TFSI⁻ by using Lithium trifluoromethanesulfonyl imide (LiTFSI). With the ether-bridged dication shown in FIG. 1, only a small amount (less than 1 wt %) in the ionic liquid electrolyte is added for improving the ionic conductivity of the ionic liquid electrolyte. As shown in FIG. 2, the ionic conductivities of the ionic liquid electrolytes made of [$C_6O_2(MIm)_2$]-$TFSI_2$ and EMIm-TFSI (1-ethyl-3-methylimidazolium bis(trifluoromethanesulfonyl)imide) as the comparison groups, respectively, and the ionic conductivity of an ionic liquid electrolyte with 5 wt % [$C_6O_2(MIm)_2$]-$TFSI_2$ in EMIm-TFSI (mixture group) according to one embodiment of the present invention, are measured. From FIG. 2, compared with the comparison groups ([$C_6O_2(MIm)_2$]-$TFSI_2$ and EMIm-TFSI), the mixture group still has the ionic conductivity at −20° C.; the ionic conductivity can reach around 2.5 mS/cm at 20° C., which is about 30% higher than that of EMIm-TFSI group; the enhancement is at least 80% at 60° C., and the ionic conductivity can reach over 4.5 mS/cm.

Figure 3:
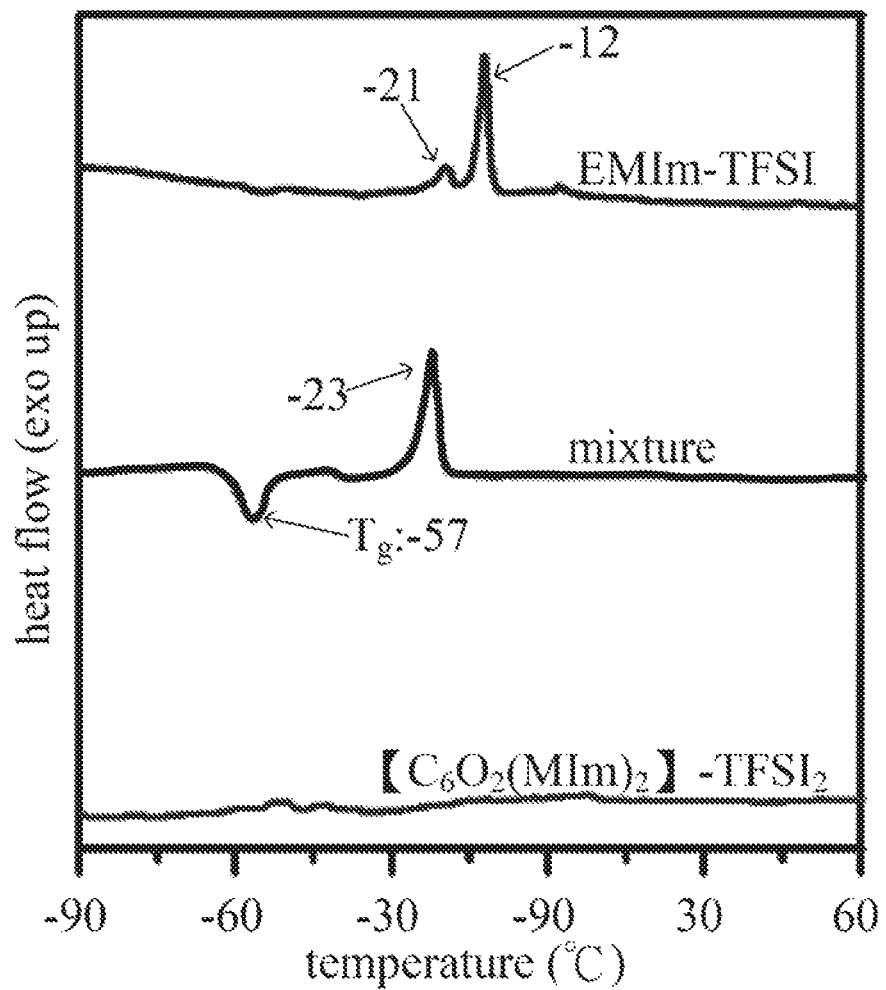
FIG. 3 shows a DSC result of the ionic liquid electrolyte (EMIm-TFSI+[$C_6O_2(MIm)_2$]) according to one embodiment of the present invention.

Furthermore, as shown in FIG. 3, the DSC (Differential Scanning Calorimetry) test shows that the chemical stability of the dication [$C_6O_2(MIm)_2$]-$TFSI_2$ is excellent. There is no obvious freezing phenomenon at −90° C., and the freezing point of the mixture can be lowered, and thus the conductivity can be maintained in an environment of −20° C. In addition, the mixture contains no organic solvent so as to avoid the safety problems caused by its high volatility, such as explosion or fire. Therefore, the cycle time of the ionic liquid electrolyte, or the cycle time of the element with the ionic liquid electrolyte can be improved.

Figure 4A:
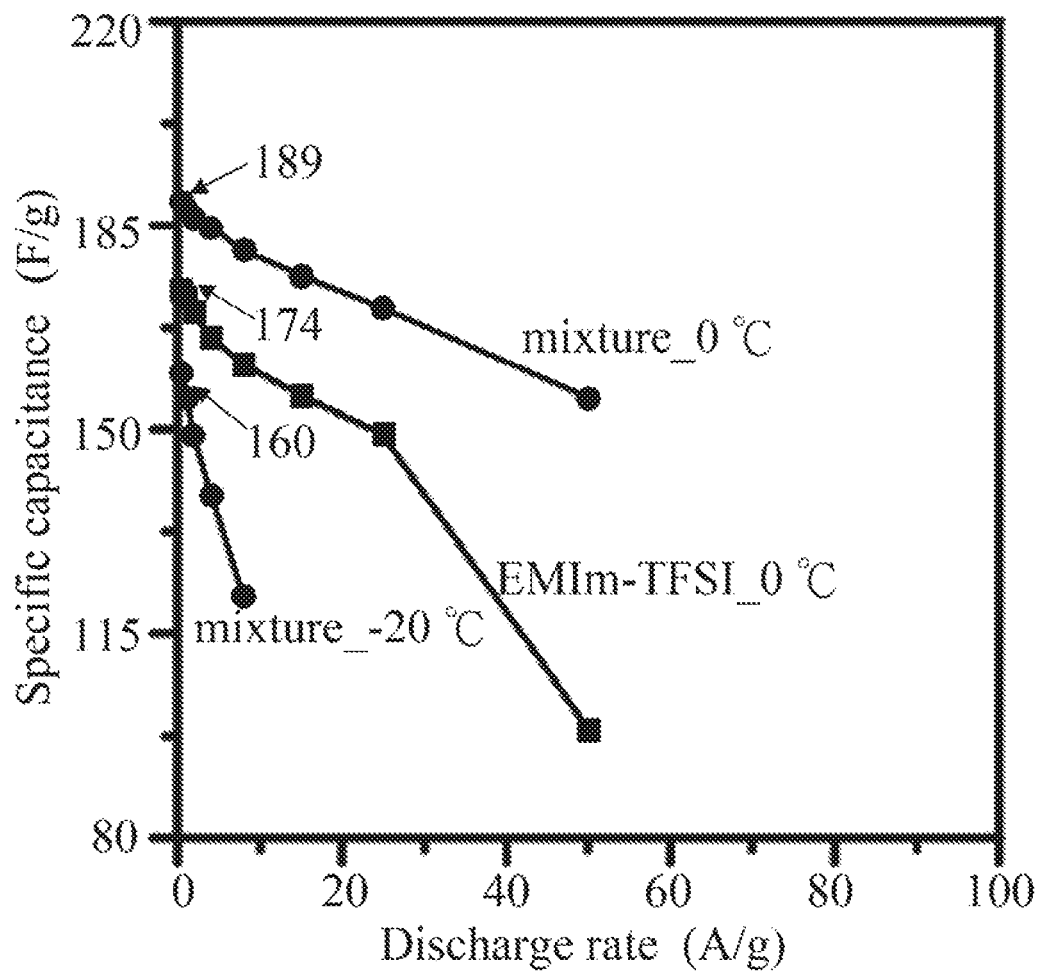
FIGS. 4A and 4B show specific capacities of super capacitors produced by the ionic liquid electrolyte (EMIm-TFSI+[$C_6O_2(MIm)_2$]) according to one embodiment of the present invention and the ionic liquid electrolyte (EMIm-TFSI) of the control group at different temperature.
Figure 4B:
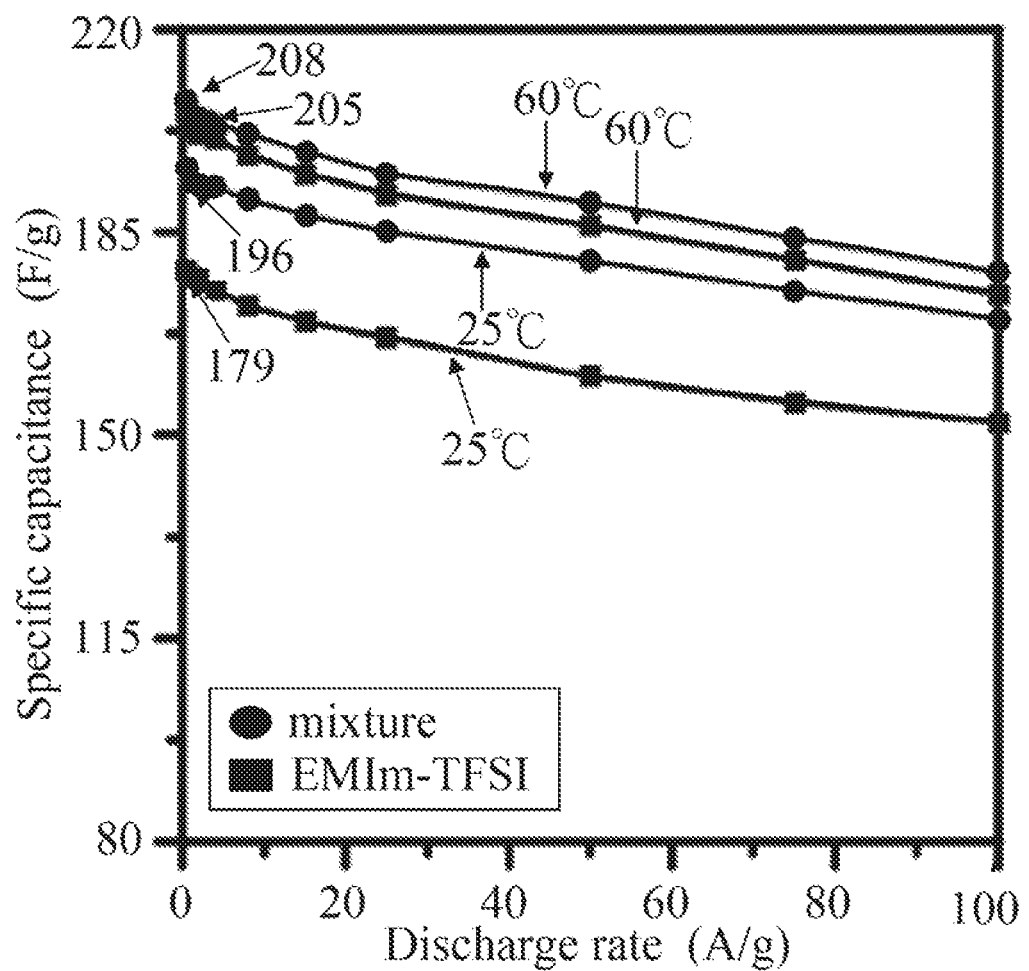
Figure 5:
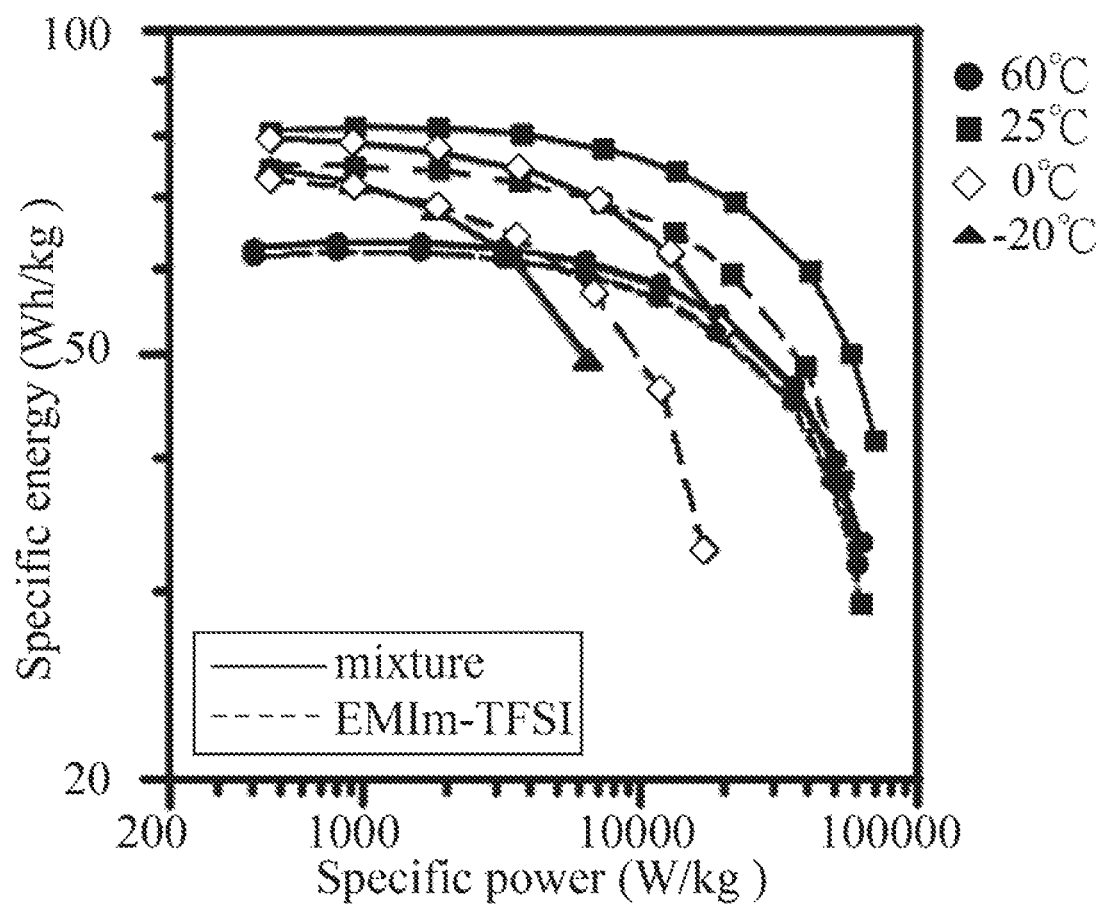
FIG. 5 shows specific energies at different temperatures of the ionic liquid electrolyte (EMIm-TFSI+[$C_6O_2(MIm)_2$]) according to one embodiment of the present invention and the ionic liquid electrolyte (EMIm-TFSI) of the control group.

A further embodiment of the present invention provides a charge storage device having the abovementioned ionic liquid electrolyte. The charge storage device can be a super capacitor (or double layer capacitor) formed by the ionic liquid electrolyte and a high porosity activated carbon. As shown in FIGS. 4A and 4B, the super capacitor according to the present invention has a specific capacitance more than 160 F/g at a discharge rate of 0.5 A/g at −20° C., and up to 208 F/g at 60° C. In addition, as shown in FIG. 5, the working potential (potential window) of the ionic liquid electrolyte according to the present invention has a maximum value of 3.5 V when the specific power is 20000 W/kg, the specific energy reaches 70 Wh/kg.

Compared to the traditional technologies, the ether-bridged dication of the present invention can bond two monovalent cations through a carbon chain having ether group(s) to form a flexible molecule. The ether group allows the dication to be more flexible. The oxygen (O) in the ether group can form hydrogen bonds when mixing with the monovalent cation to form the ionic liquid electrolyte, so as to improve the chemical stability of the ionic liquid electrolyte, and provide excellent capacitor characteristics in a wide temperature range.

The present invention has been described with preferred embodiments thereof and it is understood that many changes and modifications to the described embodiments can be carried out without departing from the scope and the spirit of the invention that is intended to be limited only by the appended claims.

What is claimed is:

1. An ionic liquid electrolyte, comprising:
   an ether-bridged dication;
   at least one monovalent cation; and
   at least one anion;
   wherein the ionic liquid electrolyte is formed without organic solvents;
   wherein the ether-bridged dication has two monovalent cations represented by $X_1$ and $X_2$, and the monovalent cations are bonded through a carbon chain having at least one ether group, wherein the ether-bridged dication has the molecular structure given as follows:

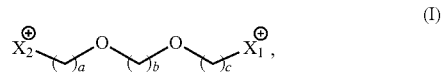

(I)

wherein at least one $X_1$ and $X_2$ is an alkyl sulfonium cation or an alkyl phosphonium cation; and each of a, b, and c is an integral selected from 1 to 10, wherein the ether-bridged dication is 2-20 wt % of the of the ionic liquid electrolyte, and wherein at least one of $X_1$ and $X_2$ is the alkyl sulfonium cation.

2. The ionic liquid electrolyte according to claim 1, wherein the anion is selected from a group consisting of [$BF_4$]$^-$, [$PF_6$]$^-$, a Bis(fluorosulfonyl)imide anion, and a Bis(trifluorosulfonyl)imide anion.

* * * * *